US010792491B2

(12) United States Patent
    Feldman et al.

(10) Patent No.: US 10,792,491 B2
(45) Date of Patent: Oct. 6, 2020

(54) PULSED PASSIVE CHARGE RECOVERY CIRCUITRY FOR AN IMPLANTABLE MEDICAL DEVICE

(71) Applicant: Boston Scientific Neuromodulation Corporation, Valencia, CA (US)

(72) Inventors: Emanuel Feldman, Simi Valley, CA (US); Jordi Parramon, Valencia, CA (US); Goran N. Marnfeldt, Valencia, CA (US); Adam T. Featherstone, Meridian, ID (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 294 days.

(21) Appl. No.: 15/799,499

(22) Filed: Oct. 31, 2017

(65) Prior Publication Data

US 2018/0140831 A1    May 24, 2018

Related U.S. Application Data

(60) Provisional application No. 62/425,768, filed on Nov. 23, 2016.

(51) Int. Cl.
    *A61N 1/05*     (2006.01)
    *A61N 1/36*     (2006.01)
    (Continued)

(52) U.S. Cl.
    CPC ......... *A61N 1/0551* (2013.01); *A61N 1/0534* (2013.01); *A61N 1/3605* (2013.01);
    (Continued)

(58) Field of Classification Search
    CPC .......................... A61N 1/375; A61N 1/36125
    See application file for complete search history.

(56) References Cited

U.S. PATENT DOCUMENTS 6,181,969 B1   1/2001  Gord
6,516,227 B1   2/2003  Meadows et al.
(Continued)

OTHER PUBLICATIONS

International Search Report and Written Opinion regarding corresponding PCT Application No. PCT/US2017/059560, dated Jan. 30, 2018.

(Continued)

*Primary Examiner* — Alyssa M Alter
(74) *Attorney, Agent, or Firm* — Lewis & Reese, PLLC

(57) ABSTRACT

The problem of a potentially high amount of supra-threshold charge passing through the patient's tissue at the end of an Implantable Pulse Generator (IPG) program is addressed by circuitry that periodically dissipates only small amount of the charge stored on capacitances (e.g., DC-blocking capacitors) during a pulsed post-program recovery period. This occurs by periodically activating control signals to turn on passive recovery switches to form a series of discharge pulses each dissipating a sub-threshold amount of charge. Such periodic pulsed dissipation may extend the duration of post-program recovery, but is not likely to be noticeable by the patient when the programming in the IPG changes from a first to a second program. Periodic pulsed dissipation of charge may also be used during a program, such as between stimulation pulses.

20 Claims, 11 Drawing Sheets

(51) Int. Cl.
  *A61N 1/375* (2006.01)
  *A61N 1/08* (2006.01)
  *A61N 1/372* (2006.01)

(52) U.S. Cl.
  CPC ..... *A61N 1/36125* (2013.01); *A61N 1/36146* (2013.01); *A61N 1/375* (2013.01); *A61N 1/08* (2013.01); *A61N 1/36014* (2013.01); *A61N 1/3752* (2013.01); *A61N 1/37217* (2013.01)

(56) References Cited

U.S. PATENT DOCUMENTS

| | | |
|---|---|---|
| 7,076,307 B2 | 7/2006 | Boveja et al. |
| 7,127,298 B1 | 10/2006 | He et al. |
| 7,881,803 B2 | 2/2011 | Parramon et al. |
| 8,606,362 B2 | 12/2013 | He et al. |
| 8,620,436 B2 | 12/2013 | Parramon et al. |
| 8,768,453 B2 | 7/2014 | Parramon et al. |
| 9,002,465 B2 | 4/2015 | Ranu |
| 9,008,790 B2 | 4/2015 | Griffith et al. |
| 9,061,140 B2 | 6/2015 | Shi et al. |
| 9,174,051 B2 | 11/2015 | Marnfeldt et al. |
| 9,259,574 B2 | 2/2016 | Aghassian et al. |
| 9,308,373 B2 | 4/2016 | Lee |
| 9,314,632 B2 | 4/2016 | Marnfeldt et al. |
| 9,737,713 B2 * | 8/2017 | Parramon .......... A61N 1/37205 |
| 2005/0131484 A1 | 6/2005 | Boveja et al. |
| 2010/0211132 A1 | 8/2010 | Nimmagadda et al. |
| 2011/0093043 A1 | 4/2011 | Torgerson et al. |
| 2011/0264171 A1 | 10/2011 | Torgerson et al. |
| 2012/0095529 A1 | 4/2012 | Parramon et al. |
| 2013/0184794 A1 | 7/2013 | Feldman et al. |
| 2013/0289661 A1 | 10/2013 | Griffith et al. |
| 2014/0266375 A1 | 9/2014 | Feldman et al. |
| 2014/0277267 A1 | 9/2014 | Vansickle et al. |
| 2015/0157861 A1* | 6/2015 | Aghassian ......... A61N 1/36125 607/2 |
| 2016/0051825 A1 | 2/2016 | Ter-Petrosyan et al. |
| 2016/0144183 A1 | 5/2016 | Marnfeldt |
| 2016/0151622 A1 | 6/2016 | Parramon et al. |
| 2016/0184591 A1 | 6/2016 | Feldman et al. |

OTHER PUBLICATIONS

U.S. Appl. No. 15/695,965, filed Sep. 5, 2017, Weerakoon et al.
U.S. Appl. No. 15/695,999, filed Sep. 5, 2017, Feldman et al.
U.S. Appl. No. 15/696,031, filed Sep. 5, 2017, Weiss et al.

* cited by examiner

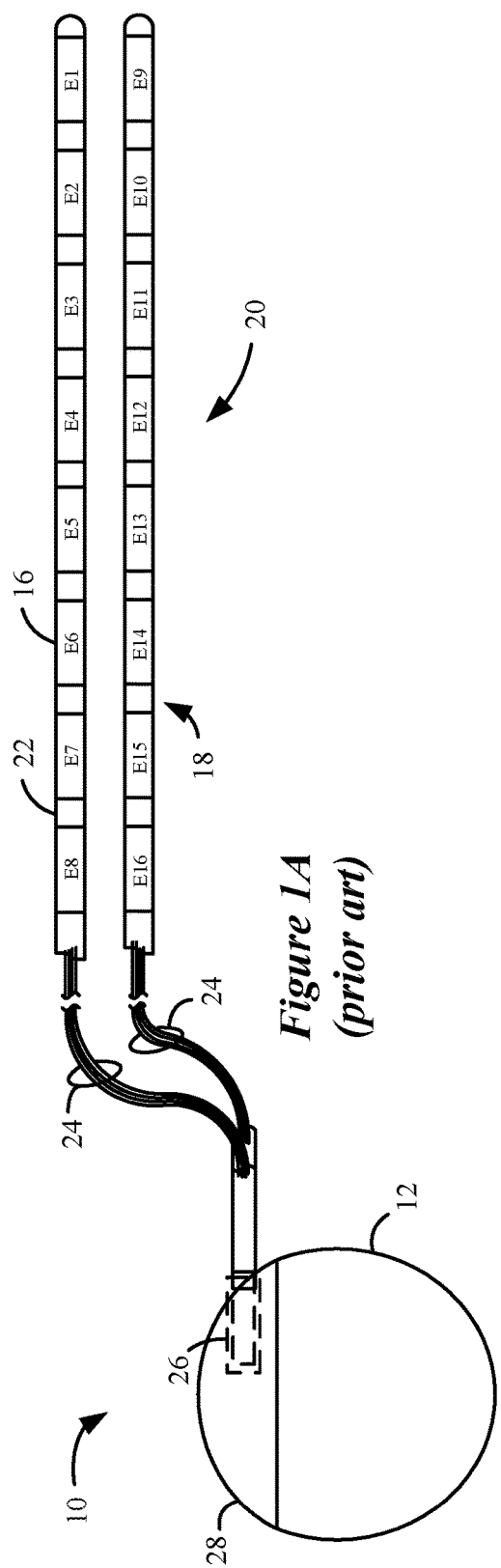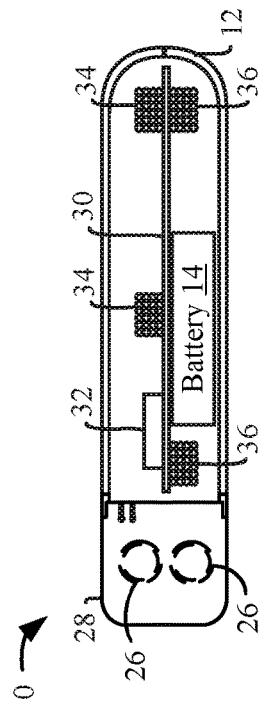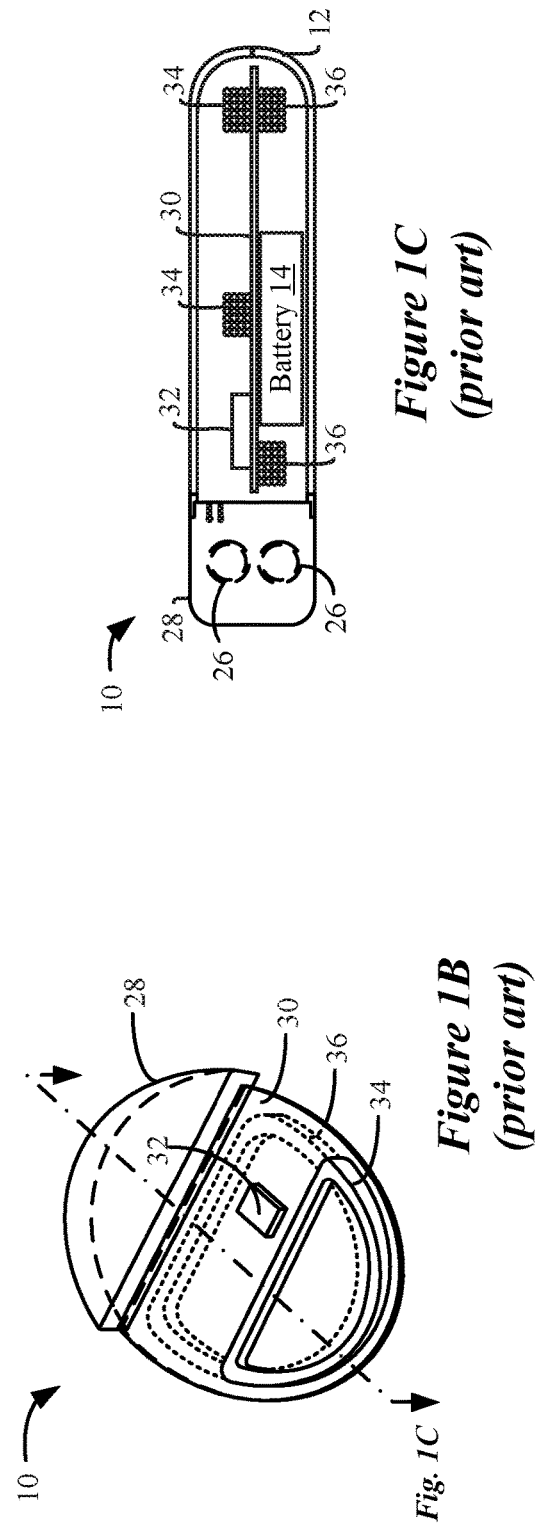
Figure 1A (prior art)
Figure 1B (prior art)
Figure 1C (prior art)

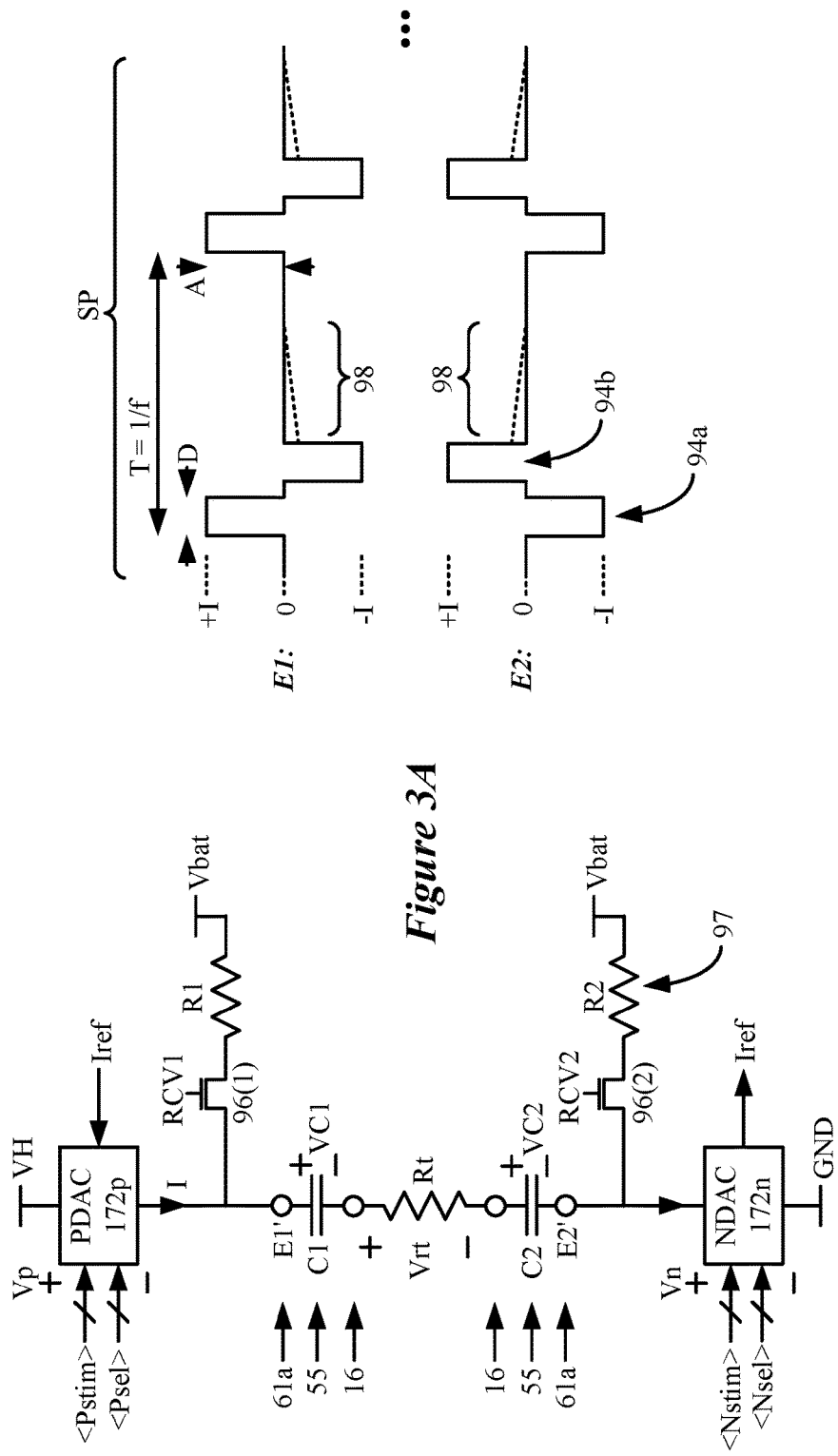
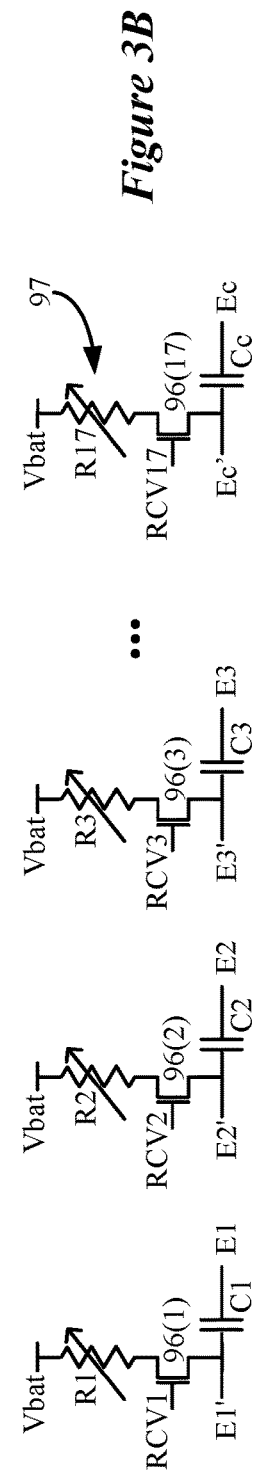
*Figure 3A*
*Figure 3B*

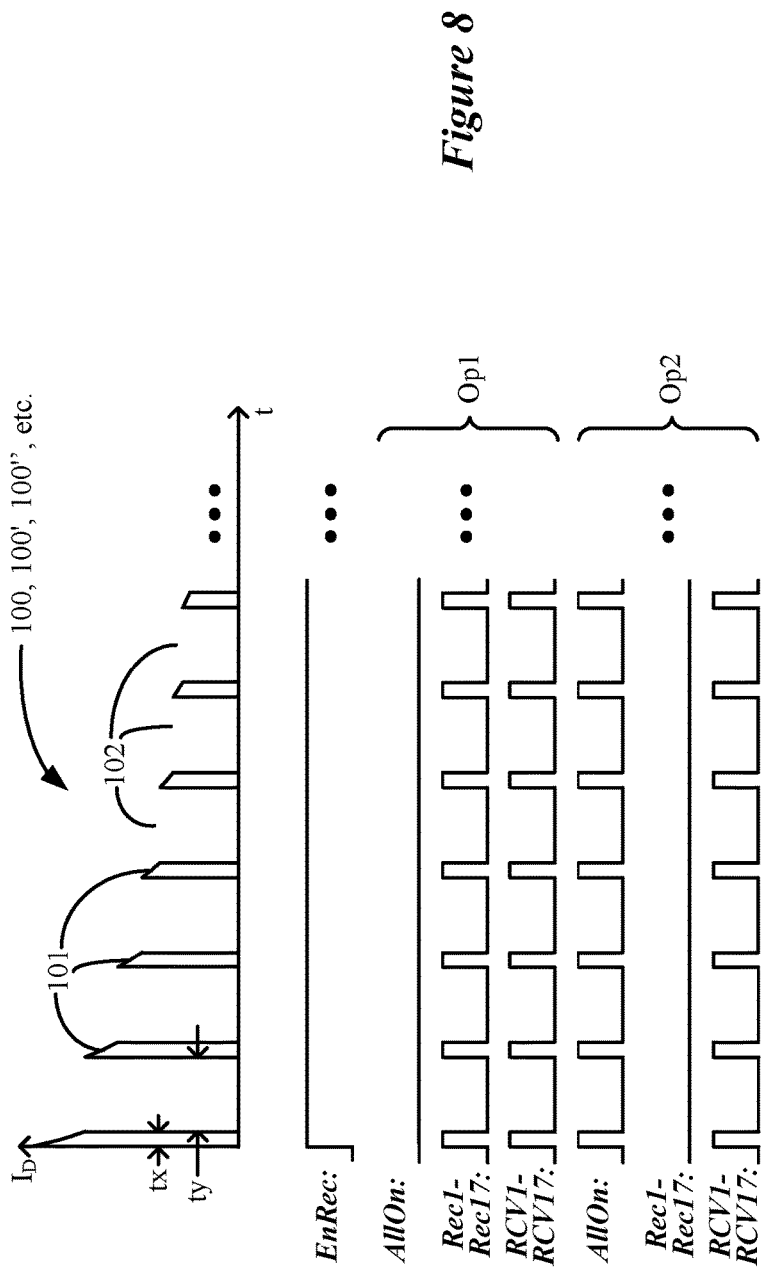

PULSED PASSIVE CHARGE RECOVERY CIRCUITRY FOR AN IMPLANTABLE MEDICAL DEVICE

CROSS-REFERENCE TO RELATED APPLICATIONS

This is a non-provisional application of U.S. Provisional Patent Application Ser. No. 62/425,768, filed Nov. 23, 2016, which is incorporated herein by reference in its entirety, and to which priority is claimed.

FIELD OF THE INVENTION

The present invention relates generally to implantable medical devices, and more particularly to improved current generation architectures for an implantable pulse generator.

INTRODUCTION

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability in any implantable medical device system, including a Deep Brain Stimulation (DBS) system.

As shown in FIGS. 1A-1C, an SCS system typically includes an Implantable Pulse Generator (IPG) 10 (Implantable Medical Device (IMD) 10 more generally), which includes a biocompatible device case 12 formed of a conductive material such as titanium for example. The case 12 typically holds the circuitry and power source (e.g., battery) 14 (FIG. 1C) necessary for the IPG 10 to function, although IPGs can also be powered via external RF energy and without a battery. The IPG 10 is coupled to electrodes 16 via one or more electrode leads 18, such that the electrodes 16 form an electrode array 20. The electrodes 16 are carried on a flexible body 22, which also houses the individual signal wires 24 coupled to each electrode. In the illustrated embodiment, there are eight electrodes (Ex) on two leads 18 for a total of sixteen electrodes 16, although the number of leads and electrodes is application specific and therefore can vary. The leads 18 couple to the IPG 10 using lead connectors 26, which are fixed in a non-conductive header material 28, which can comprise an epoxy for example.

As shown in the cross-section of FIG. 1C, the IPG 10 typically includes a printed circuit board (PCB) 30, along with various electronic components 32 mounted to the PCB 30, some of which are discussed subsequently. Two coils (more generally, antennas) are shown in the IPG 10: a telemetry coil 34 used to transmit/receive data to/from an external controller (not shown); and a charging coil 36 for charging or recharging the IPG's battery 14 using an external charger (not shown). FIG. 1B shows these aspects in perspective with the case 12 removed for easier viewing. Telemetry coil 34 may alternatively comprise a short range RF antenna for wirelessly communicating in accordance with a short-range RF standard such as Bluetooth, WiFi, MICS, Zigbee, etc., as described in U.S. Patent Application Publication 2016/0051825.

FIGS. 2A and 2B show an architecture 140 for the circuitry in IPG 10, which is disclosed in U.S. patent application Ser. Nos. 15/696,031 and 15/695,965, filed Sep. 5, 2017, which are incorporated by reference in their entireties. Architecture 140 includes at least one Application Specific Integrated Circuit (ASIC) 160. ASIC 160 includes a microcontroller block 150, which as shown in FIG. 2B can communicate with other functional blocks in the ASIC 160 via internal bus 192. Because ASIC 160 includes an internal microcontroller 150, an external microcontroller can be dispensed with in the improved architecture 140, simplifying IPG design and saving room within the interior of the case 12 and on the IPG's PCB 30 (FIG. 1C). In one example, the microcontroller block 150 can comprise circuitry from an ARM Cortex-M0+ Processor, which may be incorporated into the monolithic integrated circuit of the ASIC 160 by licensing various necessary circuits from the library that comprises that processor. ASIC 160 can comprise a monolithic integrated circuit formed on its own semiconductive substrates ("chip"), and may be contained in its own package and mounted to the IPG 10's PCB 30.

Microcontroller block 150 may receive interrupts independent of the bus 192 (INTx) and its communication protocol, although interrupts may also be sent to the microcontroller block 150 via the bus 192 as well. Even though ASIC 160 includes a microcontroller block 150, the ASIC 160 may still couple to an external bus 190. This can facilitate communications between the ASIC 160 and another device, such as a memory integrated circuit (not shown) or possibly another microcontroller device that might be coupled to the bus 190 as explained in the above-incorporated '031 and '965 Applications. Bus 190 can also facilitate communication between (master) ASIC 160 and another identically-constructed (slave) ASIC 160', shown in dotted lines in FIG. 2A. Use of an additional ASIC 160' allows the number of electrodes 16 the IPG 10 supports to be doubled, for example from sixteen to thirty two, or thirty two to sixty four. Off-bus connections 54 can facilitate master/slave interaction between ASICs 160 and 160', and as explained in detail in the above-incorporated '031 and '965 Applications.

FIG. 2B shows various functional circuit blocks within ASIC 160 in additional to the microcontroller block, which are briefly described. As mentioned, ASIC 160 includes an internal bus 192, and each of the functional blocks includes interface circuitry 88 enabling communication on the internal bus 192. Interface circuitry 88 helps each block recognize when microcontroller block 150 is communicating addresses pertaining to that block via bus 192.

ASIC 160 contains several terminals 61 (e.g., pins, bond pads, solder bumps, etc.), such as those necessary to connect to the external bus 190, the battery 14, the coils 34, 36, external memory (not shown), etc. ASIC terminals 61 include electrode nodes 61a (E1'-E16' and Ec') which circuit nodes are also present on the PCB 30 (FIG. 1C) inside of the IPG's case 12. The electrode nodes 61a connect to the electrodes 16 (E1-E16) on the lead(s) 18 outside of the case 12 by way of DC-blocking capacitors 55. As is known, DC-blocking capacitors 55 are useful to ensure that DC current isn't inadvertently (e.g., in the event of failure of the ASIC 160's circuitry) injected into the patient's tissue, and hence provide safety to the IPG 10. Such DC-blocking capacitors 55 can be located on or in the IPG 10's PCB 30. See U.S. Patent Application Publication 2015/0157861.

Note that there is also an electrode node 61a Ec' which is connected to the case 12 (preferably by a DC-blocking capacitor 55), thus allowing the case 12 to operate as an electrode 16 (Ec). ASIC 160 may support other numbers or types of electrode nodes/electrodes (e.g., thirty-two electrodes E1-E32 plus the case Ec).

Each of the circuit blocks in ASIC 160 performs various functions in IPG 10. Telemetry block 64 couples to the IPG telemetry coil 34, and includes transceiver circuitry for wirelessly communicating with an external device according to a telemetry protocol. Such protocol may comprise Frequency Shift Keying (FSK), Amplitude Shift Keying (ASK), or various short-range RF standards such as those mentioned above. Charging/protection block 62 couples to the IPG charging coil 38, and contains circuitry for rectifying power wirelessly received from an external charger (not shown), and for charging the battery 14 in a controlled fashion.

Analog-to-Digital (A/D) block 66 digitizes various analog signals for interpretation by the IPG 10, such as the battery voltage Vbat or voltages appearing at the electrodes, and is coupled to an analog bus 67 containing such voltages. A/D block 66 may further receive signals from sample and hold block 68, which can be used to measure such voltages, or differences between two voltages. For example, sample and hold circuitry 68 may receive voltages from two electrode nodes and provide a difference between them, which difference voltage may then be digitized at A/D block 66. Knowing the difference in voltage between two electrodes when they pass a constant current allows for a determination of the (tissue) resistance between them, which is useful for a variety of reasons.

Sample and hold block 68 may also be used to determine one or more voltage drops across the DAC circuitry 172 (see Vp and Vn in FIG. 3A, explained subsequently) used to create the stimulation pulses. This is useful to setting the compliance voltage VH to be output by a compliance voltage generator block 76. Compliance voltage VH powers the DAC circuitry 172, and the measured voltage drops can be used to ensure that the compliance voltage VH produced is optimal for the stimulation current to be provided—i.e., VH is not too low to be unable to produce the current required for the stimulation, nor too high so as to waste power in the IPG 10. Measuring Vp and Vn to determine whether VH is too high or too low is particularly useful because the resistance Rt of the patient's tissue may not be known in advance, or may change over time. Thus, the voltage drop across the tissue, Vrt, may change as well, and monitoring Vp and Vn provides an indication of such changes, and hence whether VH should be adjusted. Compliance voltage generator block 76 includes circuitry for boosting a power supply voltage such as the battery voltage, Vbat, to a proper level for VH. Such boost circuitry (some of which may be located off chip) can include an inductor-based boost converter or a capacitor-based charge pump, which are described in detail in U.S. Patent Application Publication 2010/0211132.

Clock generation block 74 can be used to generate a clock for the ASIC 160 and communication on the bus 192. Clock generation block 74 may receive an oscillating signal from an off-chip crystal oscillator 56, or may comprise other forms of clock circuitry located completely on chip, such as a ring oscillator. U.S. Patent Application Publication 2014/0266375 discloses another on-chip circuit that can be used to generate a clock signal on the ASIC 160.

Master/slave control block 86 can be used to inform the ASIC 160 whether it is to be used as a master ASIC or as a slave ASIC (e.g., 160 or 160' in FIG. 2A), which may be bond programmed at M/S terminal 61. For example, M/S terminal may be connected to a power supply voltage (e.g., Vbat) to inform ASIC 160 that it will operate as a master ASIC, or to ground to inform that it will operate as a slave 160', in which case certain function blocks will be disabled, as the above-cited references explain.

Nonvolatile memory (NOVO) block 78 caches any relevant data in the system (such as log data). Additional memory (not shown) can also be provided off-chip via a serial interface block 84.

ASIC 160 further includes a stimulation circuitry block 170 (FIG. 2B), which includes circuitry for receiving and storing stimulation parameters from the microcontroller block 150 via bus 192. Stimulation parameters define the shape and timing of stimulation pulses to be formed at the electrodes, and can include parameters such as which electrodes E1-E16 or Ec will be active; whether those active electrodes are to act as anodes that source current to a patient's tissue, or cathodes that sink current from the tissue; and the amplitude (A), duration (D), and frequency (f) of the pulses. Amplitude may comprise a voltage or current amplitude. Such stimulation parameters may be stored in registers in the stimulation circuitry block 170. See, e.g., U.S. Patent Application Publications 2013/0289661; 2013/0184794. Together, these stimulation parameters comprise a stimulation program (SP).

Simulation circuitry block 170 also includes a Digital-to-Analog Converter (DAC) 172 for receiving the stimulation program from the registers and for forming the prescribed pulses at the selected electrodes. FIG. 3A shows a simple example of DAC circuitry 172 operating pursuant to a stimulation program (SP) to provide a current pulse between selected electrodes E1 and E2 and through a patient's tissue, Rt. DAC circuitry 172 as shown comprises two portions, denoted as PDAC 172p and NDAC 172n. These portions of DAC circuitry 172 are so named because of the polarity of the transistors used to build them and the polarity of the currents they provide. Thus, PDAC 172p is formed from P-channel transistors and is used to source a current +I to the patient's tissue Rt via a selected electrode E1 operating as an anode. NDAC 172n is formed of N-channel transistors and is used to sink current −I from the patient's tissue via a selected electrode E2. It is important that current sourced to the tissue at any given time equal that sunk from the tissue to prevent charge from building in the tissue, although more than one anode electrode and more than one cathode electrode may be operable at a given time.

PDAC 172p and NDAC 172n receive digital control signals from the registers in the stimulation circuitry block 170, denoted <Pstim> and <Nstim> respectively, to generate the prescribed pulses with the prescribed timing and amplitude. In the example shown, PDAC 172p and NDAC 172n comprise current sources, but could comprise voltage sources as well. The PDAC 172p and NDAC 172n along with the intervening tissue Rt complete a circuit between a power supply VH—the compliance voltage introduced earlier—and ground. As noted earlier, the compliance voltage VH is adjustable to an optimal level at compliance voltage generator block 76 (FIG. 2B) to ensure that current pulses of a prescribed amplitude can be produced without unnecessarily wasting IPG power.

The DAC circuitry 172 (PDAC 172p and NDAC 172n) may be dedicated at each of the electrodes, and thus may be activated only when its associated electrode is selected as an anode or cathode. See, e.g., U.S. Pat. No. 6,181,969. Alternatively, the current produced by one or more DACs (or one or more current sources or sinks within a DAC) may be distributed to a selected electrode by a switch matrix (not shown), in which case optional control signals <Psel> and <Nsel> would be used to control the switch matrix and establish the connection between the selected electrode and a current source or sink. See, e.g., U.S. Pat. No. 8,606,362. DAC circuitry 172 may also use a combination of these dedicated and distributed approaches. See, e.g., U.S. Pat. No. 8,620,436.

In the example waveform shown in FIG. 3A, the pulses provided at the electrodes are biphasic, meaning that each pulse comprises a first phase 94a of a first polarity, followed by a second phase 94b of an opposite polarity. This is useful as a means of active recovery of charge that may build up on the DC-blocking capacitors 55. Thus, while charge will build up on the capacitors 55 during the first pulse phase 94a, the second pulse phase 94b will actively recover that charge, particularly if the total amount of charge is equal in each phase (i.e., of the area under the first and second pulse phases are equal). Recovery of excess charge on the DC-blocking capacitors 55 is desirable to ensure that the DAC circuitry 172 will operate as intended: if the charge across the DC-blocking capacitors 55 is not zero at the end of each pulse, such remaining charge may impact formation of subsequent pulses, or other problems may occur, as discussed further below.

While active recovery of charge using a biphasic pulse is beneficial, such active recovery may not be perfect, and hence some residual charge may remain on the DC-blocking capacitors 55 even after completion of the second phase 94b of the biphasic pulse. Thus, the art has recognized the utility of passive charge recovery not involving use of active currents provided by the DAC circuitry 172. Passive charge recovery is implemented within the stimulation circuitry block 170, and includes use of passive recovery switches (e.g., transistors) 96($x$), each connected between one of the electrode nodes (Ex' and Ec') 61a and a common reference voltage, as shown in FIG. 3B. This common reference voltage as shown may simply comprise the voltage, Vbat, of the battery 14 (FIG. 1C), but another reference voltage could also be used, such as the compliance voltage VH described earlier, a midpoint voltage such as VH/2, ground (GND), or some other value.

Each passive recovery switch 96($x$) is controlled by a control signal RCVx, which control signals can issue during a passive charge recovery phase 98 after the second pulse phase 94b. As explained further below, asserting the control signals (e.g., RCV1 and RCV2) corresponding to the previously-active electrodes (e.g., E1 and E2) couples the DC-blocking capacitors 55 of those electrodes in parallel between the common reference voltage and the patient's tissue, Rt, which should passively recover any remaining charge on the capacitors. See e.g., U.S. patent application Ser. No. 15/695,999 ("the '999 Application"), filed Sep. 5, 2017, which is incorporated by reference in its entirety (discussing advents related to passive recovery).

In series with each of the passive recovery switches 96 are passive recovery resistors 97, Rx. As shown, resistors Rx are between the switches 96($x$) and the common reference voltage, but resistors Rx could also be between the switches 96($x$) and the respective electrode nodes 61a; that is, the serial connection of the switches 96($x$) and resistors Rx could be flipped. The passive recovery resistors 97 set the rate at which remaining charge on the DC-blocking capacitors 55 are discharged during the passive charge recovery phases 98. The resistance of resistors 97 may be adjustable, as explained in further detail in the above-incorporated '999 Application.

BRIEF DESCRIPTION OF THE DRAWINGS

FIGS. 1A-1C show an Implantable Pulse Generator (IPG), and the manner in which an electrode array is coupled to the IPG, in accordance with the prior art.

FIG. 3A shows aspects of the Digital-to-Analog converters within the stimulation circuitry of the ASIC, and stimulation pulses formable thereby, while FIG. 3B discloses passive recovery switches and related circuitry used during passive charge recovery phases after each stimulation pulse.

FIG. 8 shows generation of control signals usable to implement a pulsed post-program recovery period.

FIG. 9 shows use of pulsed post-program recovery period between programs operating in an IPG, which program may comprise stimulation programs or other operational IPG programs.

DETAILED DESCRIPTION

Figure 2A:
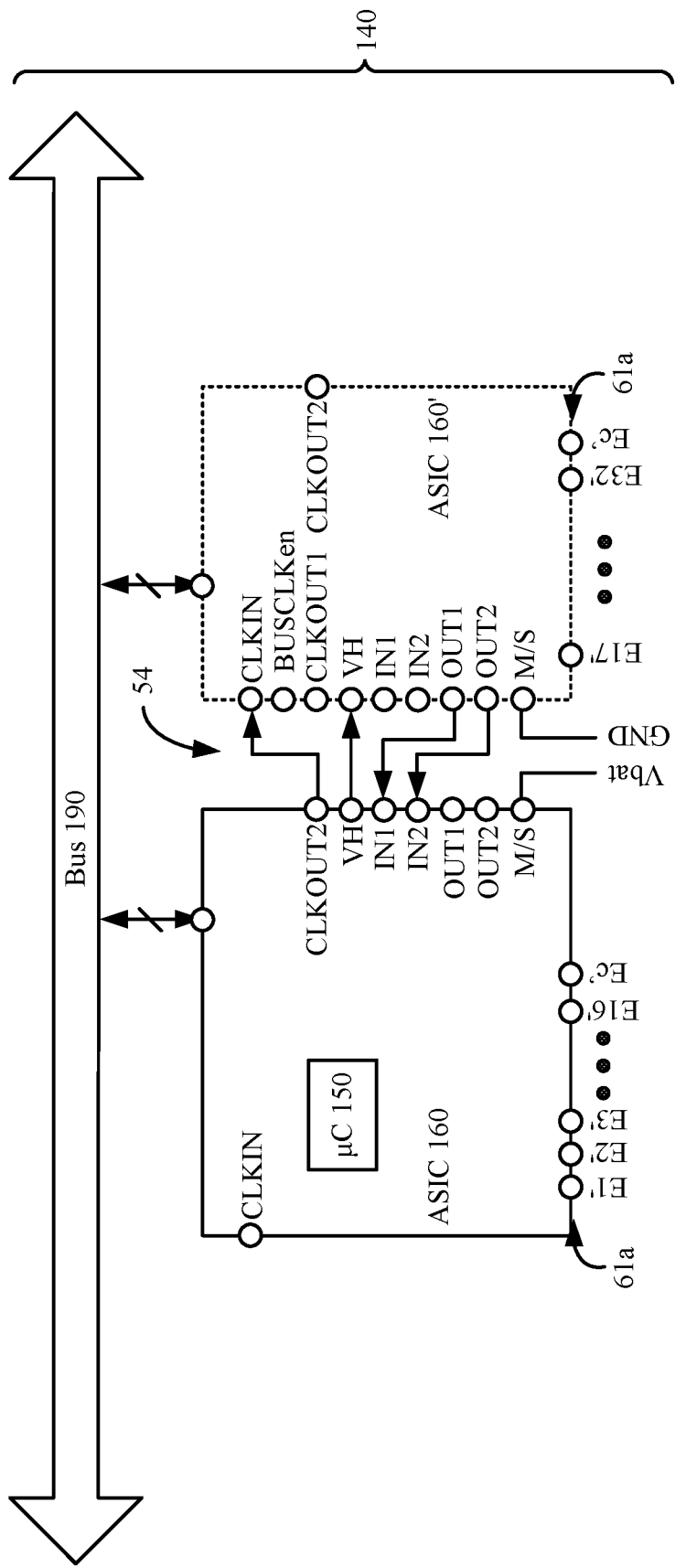
FIG. 2A shows an architecture for an IPG utilizing at least one Application Specific Integrated Circuit (ASIC)

As noted earlier, an IPG 10 may include circuitry and techniques designed to remove the charge from DC-blocking capacitors 55 in the electrode output paths that provide stimulation to a patient's tissue, Rt. An IPG 10 may issue biphasic pulses, with the second pulse phase 94b (FIG. 3A) designed to actively recover charge stored on the DC-blocking capacitors 55. Beyond this, a passive charge recovery phase 98 may be implemented to recover any remaining charge that was not recovered during active charge recovery (at the end of second pulse phase 94b).

Using both active (94b) and passive (98) charge recovery techniques, the charge Q across DC-blocking capacitors 55 in any electrode output path involved in providing stimulation is ideally zero before those electrode output paths need to issue a next pulse. In other words, the voltage across such capacitors (V=Q/C) is ideally zero at the end of each passive charge recovery phase 98.

Figure 4A:
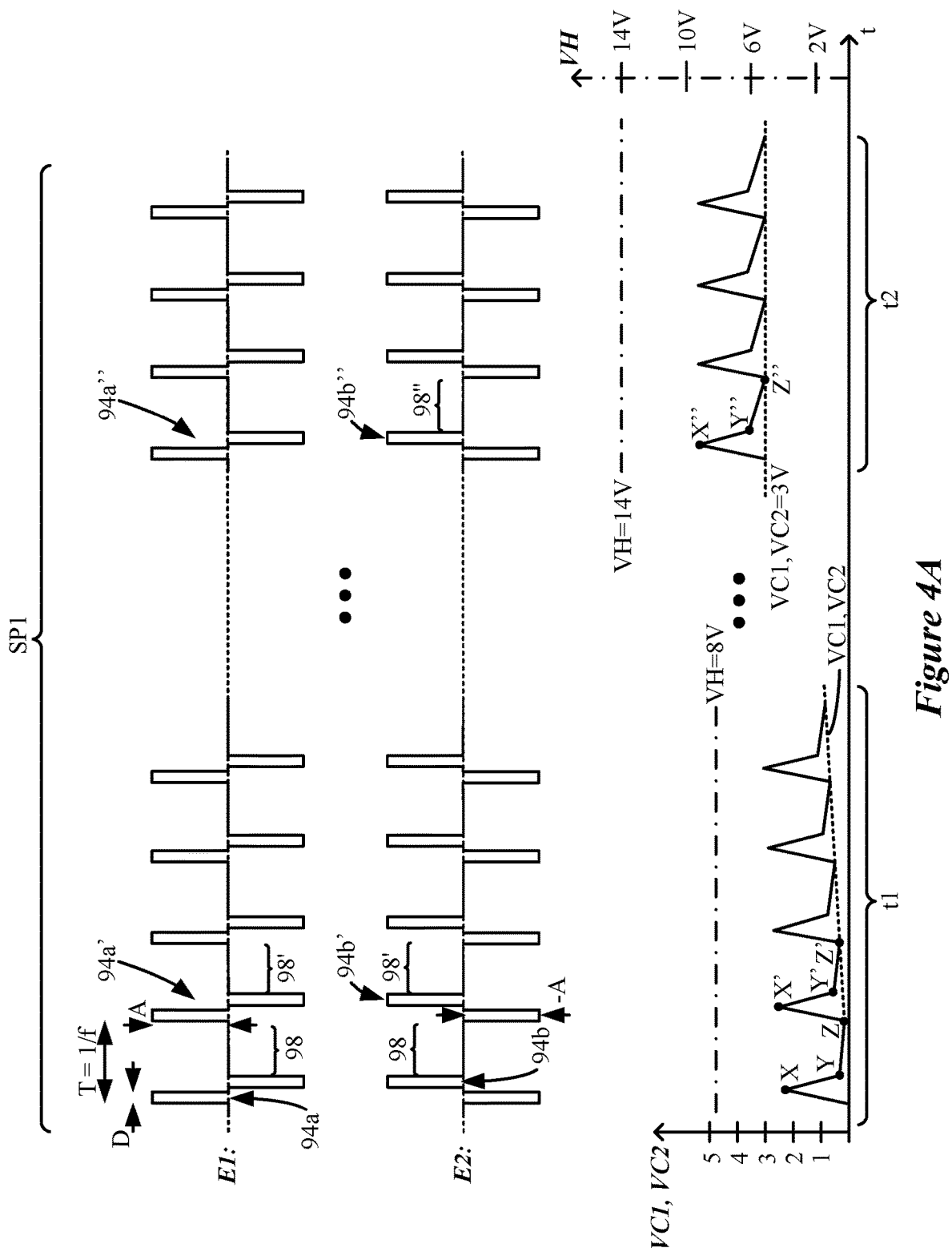
FIGS. 4A and 4B show examples of stimulation programs, and the accumulation of charge on DC-blocking capacitors despite use of passive charge recovery phases following pulses of the stimulation program.

However, the inventors realize this ideal goal is not always achievable, particularly when the DAC circuit 172 of the IPG 10 is instructed to form pulses of a high frequency, f, such as, but not limited to, ≥5 kHz. Such high frequency pulses as issued pursuant to a stimulation program (SP1) are shown in FIG. 4A, which again comprise biphasic pulses with first 94a and second 94b pulses phases. Also shown in FIG. 4A is passive charge recovery phase 98 which follows each second pulse phase 94b. Notice that because the frequency f is high, the duration of each passive charge recovery phase 98—from the end of a second pulse phase

94b of one pulse to a first pulse phase 94a of a subsequent pulse—must be relatively short. The inventors note that the duration of this phase 98 may be too short to passively recovery all charge remaining on the DC-blocking capacitors 55.

This is shown at the bottom of FIG. 4A, which shows the voltage across the DC-blocking capacitors 55 involved in providing stimulation, e.g., capacitors C1 and C2 associated with electrodes E1 and E2. After a first phase 94a of a first pulse, the voltage across each capacitor C1 and C2 (VC1 and VC2) is high (X), but is reduced to near zero (Y) after the second active-charge-recovery pulse phase 94b. A passive charge recovery phase 98 begins thereafter. However, as shown in FIG. 4A, the end of the passive charge recovery phase 98—although reducing VC1 and VC2 still further (Z)—does not bring these voltages exactly to zero.

As a result, a next pulse (with first and second phases 94a' and 94b') will not start with capacitors C1 and C2 that are completely discharged, i.e., VC1 and VC2 don't equal zero. This increases the voltage across the capacitors: X' after the first pulse phase 94a' is higher than after first pulse phase 94a X; Y' after the second pulse phase 94b' is higher than after second pulse phase 94b Y; and Z' at the end of the passive charge recovery phase 98' is higher than at the end of passive charge recovery phase 98 Z. As subsequent pulses are issued, these voltages begin to climb over time period t1, as shown by the dotted line in FIG. 4A.

Eventually, the voltages across the capacitors will increase to a steady-state condition as shown during time period t2 in FIG. 4A. In the depicted example, the voltages across the capacitors C1 and C2 are established around a new steady-state baseline voltage, such as 3V, as shown in the dotted line of t2. This baseline voltage could differ depending on the particulars. In any event, from this baseline, the voltages across the capacitors increase after a first pulse phase 94a'' (to X''), then decrease after a second pulse phase 94b'' (to Y''), and then decrease back to the baseline (to Z''=3V) at the end of a passive charge recovery phase 98''. The steady-state baseline voltage across the capacitors is reached at Z'' because—as discussed further below—the passive charge recovery phases 98 decrease the voltage across each capacitor exponentially. When the baseline voltage is high enough during time period t2, the exponential drop experienced during the passive charge recovery phases 98 are significant enough to keep the voltages from increasing, and thus allowing a steady-state to be reached.

While is it desirable that the voltages across the capacitors VC1 and VC2 be zero at the end of each second pulse phase 94b, or at least at the end of each passive charge recovery phase 98, it is not necessarily a problem that this doesn't occur, particularly if the compliance voltage VH is adjustable as it is in IPG 10. As described earlier, IPG 10 includes on ASIC 160 compliance voltage generation circuitry 76 (FIG. 2B) that produces a compliance voltage HV. Compliance voltage VH can vary during the provision of stimulation pulses, preferably in conjunction with the feedback provided by measurements such as the voltage drops across the PDAC 172p (Vp) and NDAC 172n (Vn) used in providing stimulation, as described earlier. An increase in VC1 and VC2 will cause Vp and Vn to drop for a given VH (FIG. 3A), such that Vp and Vn would now indicate that VH is too small. Thus, compliance voltage generation circuitry 76 would raise VH to compensate.

This is shown in FIG. 4A. Compliance voltage generation circuitry 76 may initially during time period t1 set VH to 8V as an example. As the voltages VC1 and VC2 across the capacitors C1 and C2 grow, compliance voltage generation circuitry 76 increases VH. Thus, during time period t2, when both VC1 and VC2 are established around a steady-state baseline of 3V, VH has been increased from 8V to 14V (to compensate for VC1+VC2=6V). To summarize, even though the voltages VC1 and VC2 across the capacitors C1 and C2 increased over time, DAC circuitry 172 is still able to output high-frequency pulses with the proper amplitude (+A, −A) by increasing the compliance voltage, VH.

Figure 4B:
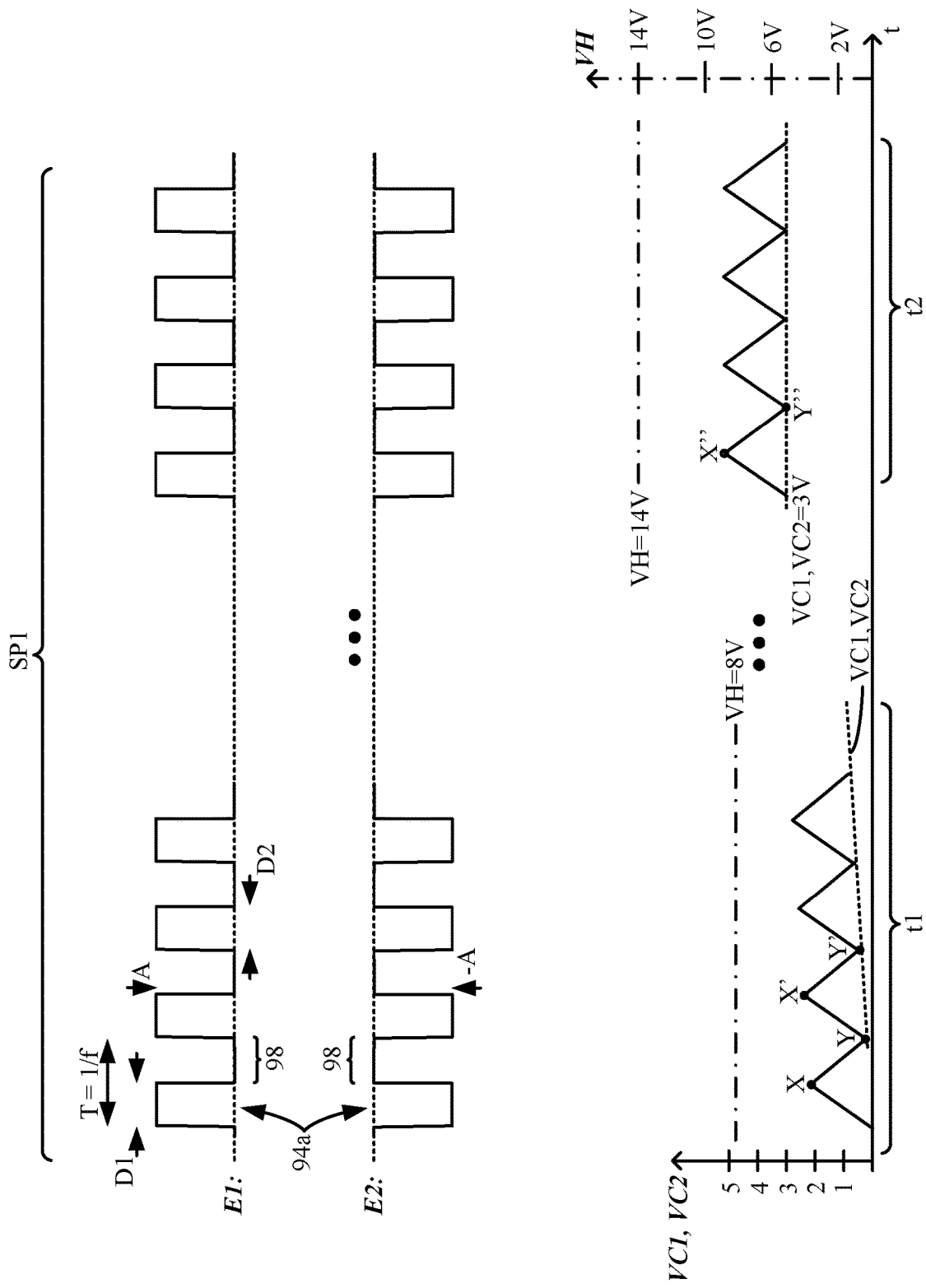

FIG. 4B shows another example of stimulation program SP1 in which charge builds on the DC-blocking capacitors 55 over time. In this example, monophasic pulses are used consisting of only a first pulse phase 94a. In between pulse phases 94a are passive recovery phases 98. This stimulation program, which lacks active recovery second pulse phases 94b (FIG. 4A), is again logical to use at high frequencies f where pulse periods T are necessarily short. Having said this, monophasic pulses can be used at lower frequencies as well. Note that the duration of the pulse phases 94a (D1) and the passive recovery phases 98 (D2) may be equal (e.g., 100 microseconds each), although they may also have different durations.

Similarly to FIG. 4A, and as shown at the bottom of FIG. 4B, the voltages (VC1, VC2) across the capacitors (C1, C2) associated with the active electrodes (E1, E2) increase during monophasic pulse phase 94a (to X), and then will exponentially decay during the passive recovery phase 98, although it does not do so perfectly as a residual voltage remains at Y. The voltages thus increase during time period t1 for subsequent pulses (e.g., X', Y'), and eventually establish at a baseline (X'' and Y'') during time period t2 as before, and with the compliance voltage increasing to compensate for the additional voltages dropped across the capacitors.

Figure 5:
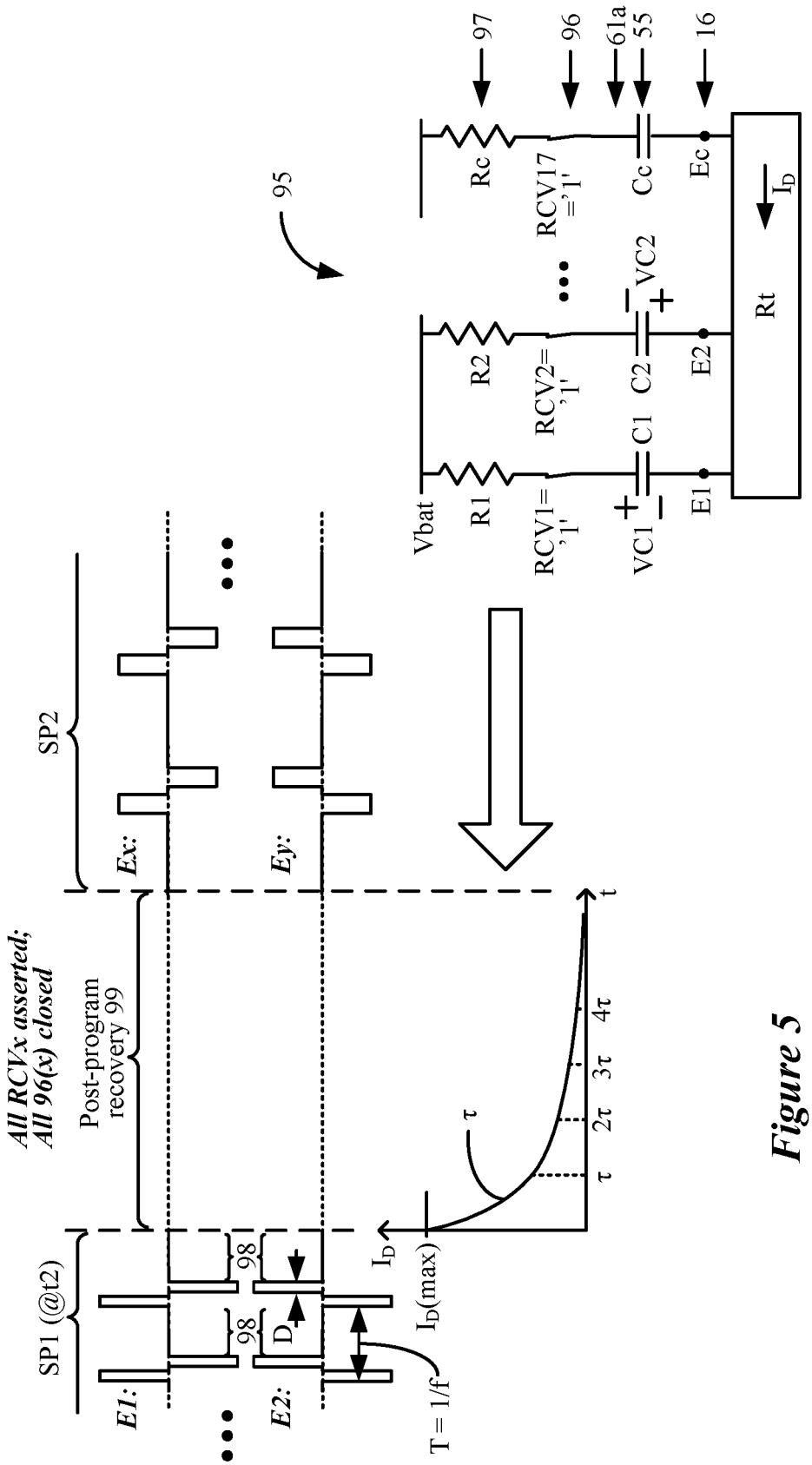
FIG. 5 shows use of a post-program passive recovery period, and the equivalent circuit formed thereby.

The fact that the DC-blocking capacitors 55 cannot be completely discharged raises concern noticed by the inventors, which are illustrated in FIG. 5. At the end of a program—such as either of the stimulation programs SP1 illustrated in FIG. 4A or 4B—the inventors find it desirable to close all of the passive recovery switches 96(x) during a post-program recovery period 99 before allowing the IPG 10 to execute a new stimulation program SP2. New program SP2 may involve wholly different stimulation parameters and electrodes, or may involve changes to the stimulation parameters and electrodes involved during program SP1, such as a change in pulse amplitude A. By way of review, closing all of passive recovery switches 96(x) can be affected by the assertion of all of control signals RCVx (FIG. 3B).

Closing all passive recovery switches 96(x) during post-program recovery period 99 at the end of a program such as SP1 is desirable in the inventors view. First, this will recover any charge that had built up on the DC-blocking capacitors 55 (e.g., C1 and C2) associated with the electrodes (e.g., E1 and E2) selected to provide stimulation during program SP1, which as just explained may be significant. Other DC-blocking capacitors 55 not associated with electrodes involved in providing stimulation during program SP1 (e.g., C3-C17) would normally have no charge stored on them, and thus no voltage across them. But this may not always be the case, and thus the inventors' preference for closing all passive recovery switches 96(x) during the post-program recovery period 99. For example, such other electrodes may have charge stored on them by virtue of being active in another timing channel different from that running stimulation program SP1. Further, an electrode may have experienced a fault, such as an open circuit, and its DC-blocking capacitor 55 may have stored charge prior to the fault.

When the passive recovery switches 96(x) are closed during post-program recovery period 99 (RCVx='1'), the equivalent circuit 95 of FIG. 5 results. Equivalent circuit 95 includes the series connection of passive recovery resistor 97 Rx and DC-blocking capacitor 55 through each switch 96x for each electrode Ex. These series connections are coupled in parallel between the common reference voltage (e.g., Vbat) and the patient's tissue (e.g., Rt). Because the capacitors may be charged to different values (e.g., VC1=VC2=3V, while other capacitors are charged to 0V), a discharge current, $I_D$, will flow through the patient's tissue, Rt, as the equivalent circuit 95 seeks to equilibrate the amount of charge across each of the DC-blocking capacitors 55. Preferably, at the end of the post-program recovery period 99, each capacitor stores little or no charge, and hence will have little or no voltage across them.

Because the equivalent circuit 95 is an RC circuit, the discharge current $I_D$ will start at a maximum ($I_D$(max)) and will exponentially decay from this value down to zero at a rate dictated by its time constant, $\tau$, as shown in FIG. 5. If we assume typical values for the components in the equivalent circuit 95 (e.g., R1=R2=300Ω; Rt=500Ω; C1=C2=5 μF) and that capacitors C1 and C2 are significantly charged as they are end the end of SP1 (e.g., VC1=VC2=3V), then the maximum discharge current $I_D$(max) may equal several mA, and the time constant $\tau$ may equal a few milliseconds. Note that to equate and/or remove all of the charge remaining on the DC-blocking capacitors 55 during the post-program recovery period 99, the duration of this period 99 is preferably significantly longer that the time constant $\tau$. For example, the duration of period 99 may be 10$\tau$, or a few tens of milliseconds in the depicted example.

How the discharge current $I_D$ will flow through the patient's tissue Rt during the post-program recovery period 99—i.e., the extent to which the discharge current will flow to or from any particular electrode Ex—will depend on different factors, such as the location of the electrodes Ex relative to one another in the patient's tissue, Rt, which electrodes are charged during time period t2 and to what extent, etc. Nonetheless, the discharge current $I_D$ can occur with a significant magnitude ($I_D$(max)) and—because $\tau$ is relatively large—for a significant amount of time. In total, a significant amount of charge may pass through the patient's tissue during the post-program recovery period 99. This discharge current $I_D$ therefore runs the risk of being supra-threshold—that is, felt by the patient. Moreover, the discharge current may be significant enough to actually cause discomfort to the patient, who may perceive the discharge current as an unwanted "zap" to their tissue.

Note that the equivalent circuit 95 of FIG. 5 may also be formed during each passive charge recovery phase 98 during program SP1 (e.g., FIGS. 4A, 4B), but this circuit is unlikely to cause patient discomfort in this context. The pulses 94a/94b formed during SP1 are high frequency (e.g., f≥5 kHz), and therefore the duration of each passive charge recovery phase 98 would be of short duration (e.g., <0.2 ms, or even less when duration D of the pulse phases 94a and 94b are considered). As such, only a small amount of charge Q (Q=I*t) would be removed from the DC-blocking capacitors 55 during each passive charge recovery phase 98. The inventors reason that removal of such a small amount of total charge from the DC-blocking capacitors 55 during such a short-duration phase 98 is sub-threshold—that is, undetectable by the patient. By contrast, the significantly long duration of the post-program recovery period 99 together with the relatively high amount of current $I_D$ passing through the patient's tissue Rt during this period 99 may be supra-threshold as already mentioned.

The inventors address the problem of a potentially high amount of supra-threshold charge passing through the patient's tissue post-program by periodically dissipating only small amount of the charge stored on the DC-blocking capacitors 55 during use of a pulsed post-program recovery period 100. This occurs by periodically activating the control signals RCVx during a post-program recovery period to form a series of discharge pulses after the end of the stimulation program, i.e., during a time period when the stimulation circuitry is not providing stimulation pulses. This will extend the duration of post-program recovery because gaps are included between the discharge pulses during which no charge is recovered from the DC-blocking capacitors 55. Nonetheless, the extended duration of pulsed post-program recovery period 100 should be tolerable, as it is not so long as to likely be noticed by the patient when the programming in the IPG 10 changes from a first to a second program.

Figure 6:
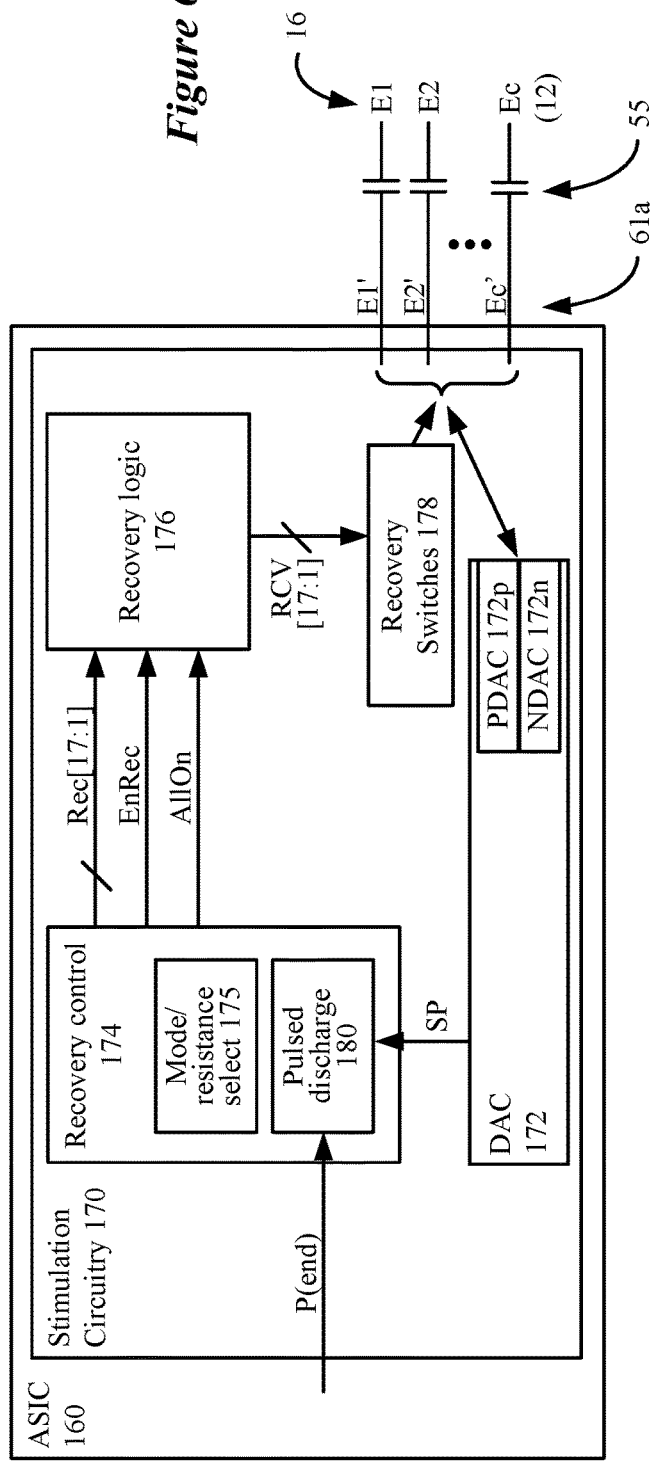
FIGS. 6A and 6B show improved passive charge recovery circuitry for the IPG, and passive recovery logic for closing passive recovery switches coupled to each of the electrode nodes.

IPG architecture 140 as introduced previously includes passive recovery circuitry used to remove charge on the DC-blocking capacitors 55 during each passive charge recovery phase 98 between pulses issued during a program. Such passive recovery circuitry has been modified to remove charge post-program—i.e., after the program has ended—during a pulsed post-program recovery period 100. FIGS. 6A and 6B show specific circuitry details. FIG. 6A shows an improved stimulation circuitry block 170 within ASIC 160, which can include the DAC circuitry 172 used to source or sink stimulation currents at the electrode nodes 61a via a PDAC 172p or NDAC 172n respectively (FIG. 3A). It is again assumed that ASIC 160 supports sixteen electrode nodes 61a E1'-E16' coupleable to sixteen electrodes 16 E1-E16 used to stimulate a patient's tissue (e.g., on lead(s) 18; see FIG. 1A), as well as a case electrode node (Ec') coupleable to a case electrode 12 (Ec). PDAC and NDAC circuitry 172p and 172n can be as described earlier, or may take other forms, or may be as disclosed in the '965 Application referenced above. Note that PDAC 172p and NDAC 172n can comprise constant current sources or constant voltage sources.

Within improved stimulation circuitry block 170 is a recovery control block 174. Recovery control block includes a mode/resistance select control module 175 that stores data used to select different passive recovery modes and different resistances Rx for the passive recovery resistors 97 (FIG. 3B). As mode and resistance adjustment is described in detail in the above-incorporated '999 Application, it is not further discussed here, although such adjustments could be used in disclosed embodiments as well.

Figure 2B:
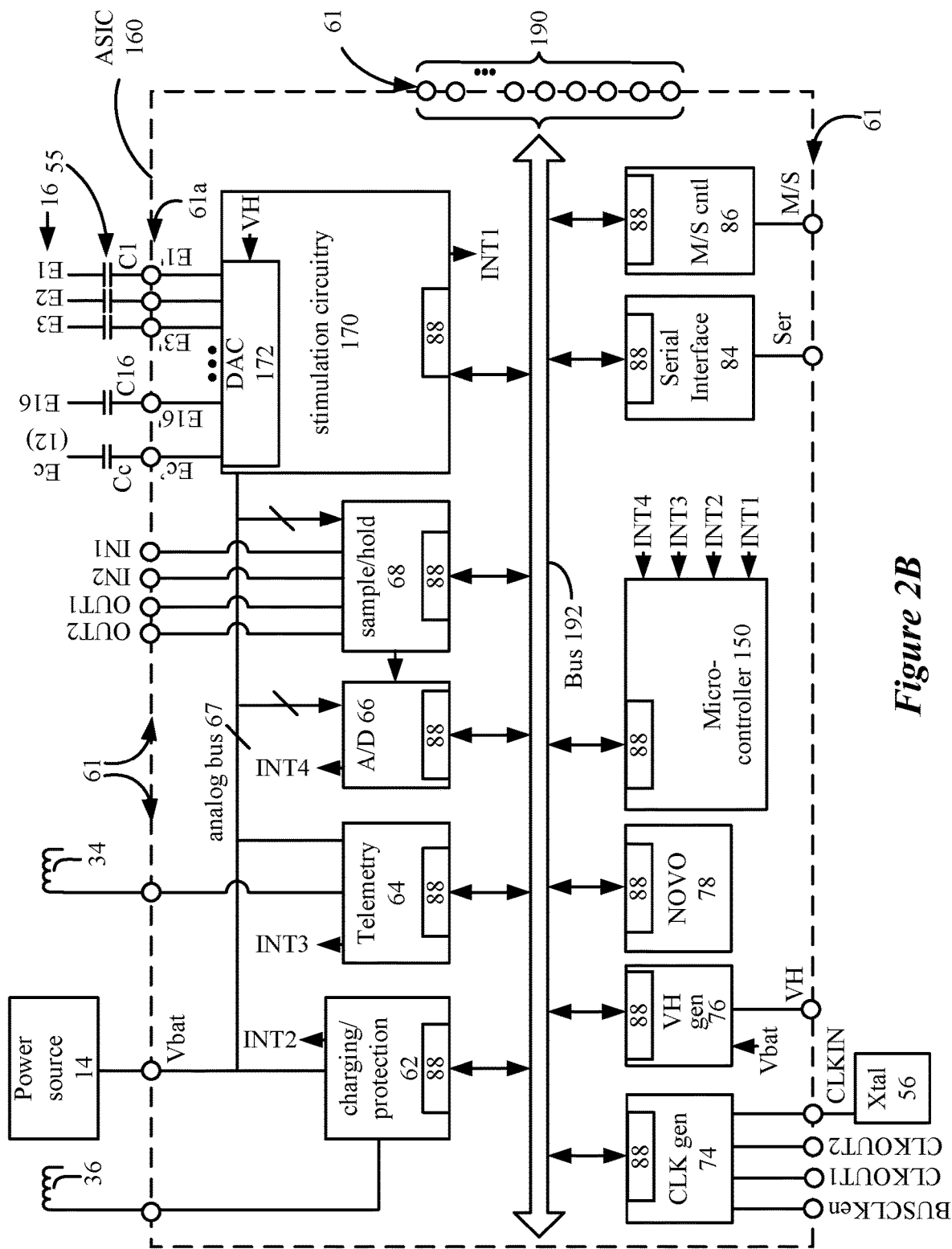
FIG. 2B shows circuitry blocks within the ASIC and connection to off-chip components.

Recovery control block 174 further includes a pulsed discharge block 180 configured to initiate and control operation of a pulsed post-program recovery period following the end of a program. The digital logic of the pulsed discharge block 180 can be made aware when the end of a program occurs in different ways. For example, pulsed discharge block 180 may receive a control signal P(end) at the end of a program. Control signal P(end) may issue from the ASIC 160—such as from the microcontroller 150 via internal bus 192 (FIG. 2B). The pulsed discharge block 180 may also understand when a program operating in the stimulation circuitry has ended, and in this regard may monitor the currently running program (SP) as shown in FIG. 6A.

The recovery control block 174—under control of blocks 175 and 180—issues control signals to recovery logic circuitry 176. These control signals include Rec[17:1], which indicate when passive recovery switches 96(x) (FIG. 3B) for the case electrode (Rec 17) and electrodes E16-E1 (Rec16-

Rec1) are to be turned on (i.e., closed). Control signal EnRec comprises a passive recovery enable signal, which as described below will enable control of the passive recovery switches 96. Control signal AllOn comprises a control signal that turns on all of the passive recovery switches 96 as described in detail later. As described in the above-incorporated '999 Application, the recovery logic 176 ultimately produce control signals RCV[17:1] each of which controls a passive recovery switch 96 (FIG. 3B) associated with the case 12 (Ec) or one of the electrodes E16-E1. FIG. 6B shows one example of logic circuitry 176, which is discussed in detail later with reference to FIG. 8.

Figure 7:
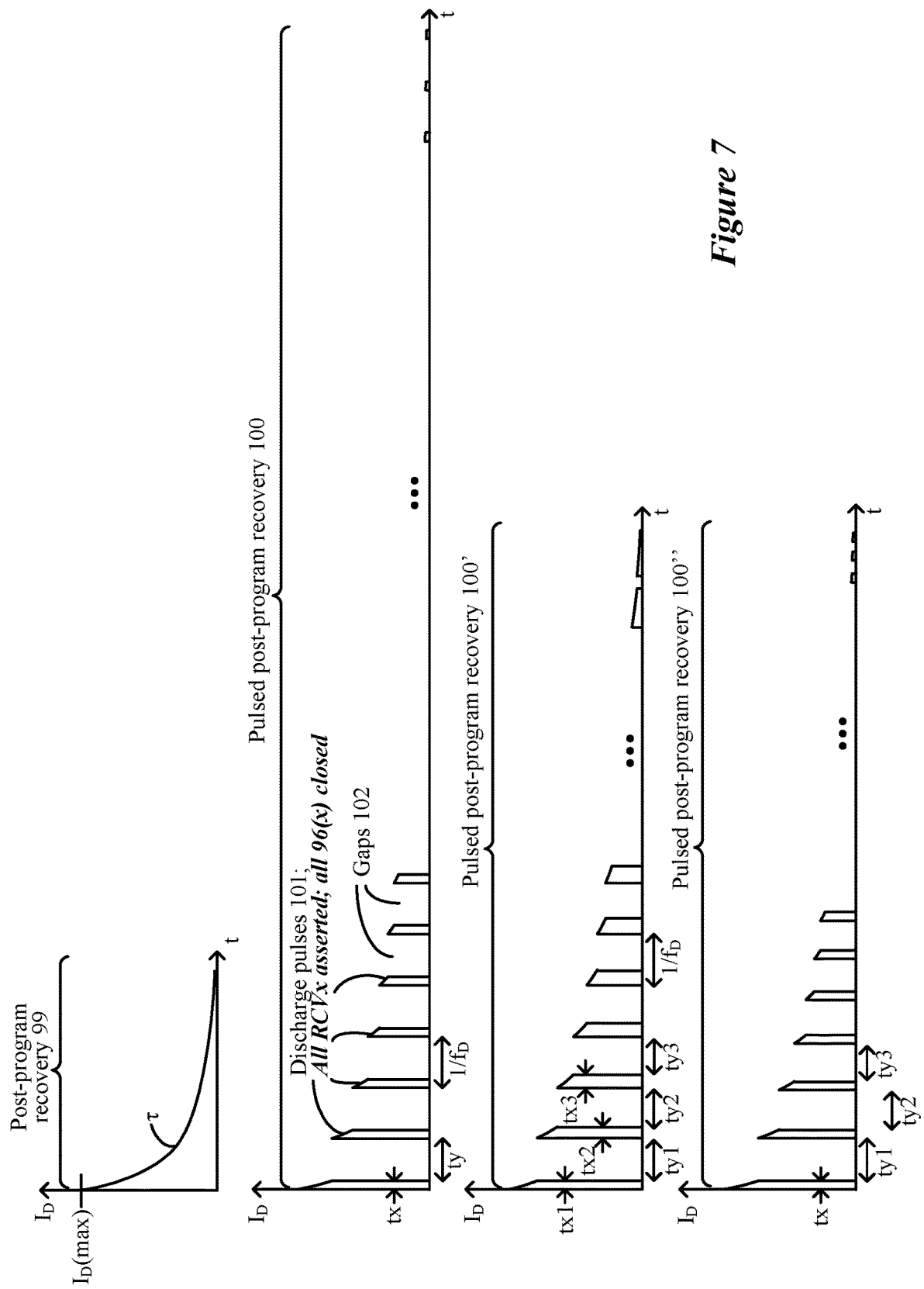
FIG. 7 shows different examples of pulsed post-program recovery periods useable after a program operating in the IPG has ended to discharge capacitance in the IPG.

FIG. 7 shows different manners in which a post-program recovery period can be controlled by the pulsed discharge block 180 in the recovery control block 174 to dissipate the charge on the DC-blocking capacitors 55 at the end of a program (e.g., SP1). The top shows the approach described earlier (FIG. 5) in which all passive recovery switches 96 are continually closed during a post-program recovery period 99. As noted earlier, this may lead to a significant and supra-threshold amount of charge being passed through the patient's tissue, Rt.

Periods 100, 100', and 100" comprise examples of pulsed post-program recovery periods, which are preferable as they periodically permit small sub-threshold amounts of charge to pass through the patient's tissue. In each of periods 100, 100' and 100", the dissipation of charge occurs periodically during discharge pulses 101, during which all passive recovery switch control signals RCVx are preferably asserted to close their associated passive recovery control switches 96. Less preferably, only the individual passive recovery switch control signals RCV associated with the previously-active electrodes during program SP1 (e.g., RCV1 and RCV2 for electrodes E1 and E2) are asserted, but this option isn't further discussed, as it would not assist in dissipating charge stored on other non-active capacitors arising from parasitic coupling from the tissue Rt as explained earlier. Between discharge pulses 101 are gaps 102 during which none of the passive recovery switch control signals RCVx are asserted, and thus all passive recovery switches 96 are opened. In other words, DC-blocking capacitors 55 are not discharged during gaps 102.

In a first example of a pulsed post-program recovery period 100, the duration of the discharge pulses 101, tx, are fixed, and the duration of the gaps 102, ty, between them are also fixed. In one example, the duration tx of the discharge pulses 101 comprises 20 microseconds or less, and the duration ty of gaps 102 comprise 500 microseconds or less. These values are preferred because it is believed that discharge through the tissue Rt of 20 microseconds or less will be sub-threshold and not felt by the patient, regardless of the magnitude of the discharge current $I_D$. In other words, the total charge passing through the patient's tissue during a discharge pulse 101 should be insignificant from a patient perception standpoint. Further rendering such stimulation imperceptible is the significant duration ty of the gaps 102 between such discharge pulses 101, which allow the tissue ample time to recover.

Note that periodic dissipation of the stored charge may lengthen the post-program recovery period. For example, if a continuous dissipation of the stored charge occurs over a period of tens of milliseconds (99), then fractionalizing this dissipation (100) will extend the length of this period by a factor of (tx+ty)/tx, which may be several hundred milliseconds for the values of tx and ty provided earlier. In other words, pulsed post-program recovery period 100 might last hundreds of milliseconds before a new program is run by the IPG 10 to ensure that the DC-blocking capacitors 55 have been discharged. While this is significantly longer than a continuous post-program recovery period 99, pulsed post-program recovery period 100 from the patient's standpoint comprises only a short delay during which the IPG 10 will transition from a first program SP1 to a new program SP2, which may not even be noticeable by the patient as a practical matter.

In second and third examples of pulsed post-program recovery periods in FIG. 7, modifications are made to reduce the time needed for recovery. In pulsed post-program recovery period 100', subsequent discharge pulses 101 are increased in duration, with duration tx2 being longer than tx1; tx3 being longer than tx2, etc. Because the discharge current $I_D$ decreases over time and hence during subsequent discharge pulses 101, increasing the duration of the discharge pulses can keep the total amount of charge (Q=I*t) relatively constant for each discharge pulse. This is especially helpful for discharge pulses 101 nearer to the end of the pulsed post-program recovery period 100', where discharge pulses 101 are low enough in current that it is significantly less risky to the patient to issue these pulses with greater durations. In the example shown, the frequency $f_D$ at which the discharge pulses 101 issue is constant; therefore, as discharge durations tx increase over time, the gap durations ty decrease over time (with ty1>ty2>ty3, etc.). Although not shown, eventually the duration tx of the discharge pulses 101 will equal that set by the frequency (1/fp), at which point the passive recovery switches 96 may be held constantly on.

It is not strictly necessary that duration ty of the gaps 102 decrease as the duration tx of the discharge pulses 101 increase. Instead, although not shown, the duration of the gaps 102 may be kept constant between the discharge pulses 101 in pulsed post-program recovery period 100'. In effect then, the discharge pulses 101 would not issue with a constant frequency, but with a frequency that decreases over the duration of the period 100'. Still, in any of these variations, because the duration tx of the discharge pulses 101 increase, the duration of the total period 100' can be smaller than for period 100.

Pulsed post-program recovery period 100" at the bottom of FIG. 7 is also of a smaller duration than period 100. However, in this example, the duration of the discharge pulses 101 are kept constant (tx), while the duration of the gaps 102 decreases over time (e.g., ty1>ty2>ty3, etc.). Thus, notice in this example that the frequency $f_D$ of the discharge pulses 101 is not constant, but increases over time. Reducing the duration ty of the gaps 102 is sensible in this example, because smaller amount of charge are discharged from the DC-blocking capacitors 55 over time. Hence, gaps 102 can be made smaller, as the patient's tissue will need less time to recover to decrease the amount of charge.

All of the above examples 100, 100' and 100" by which discharge pulses 101 are issued during a pulsed post-program recovery period can be modified or combined. What is important is that a plurality of discharge pulses issue during the pulsed post-program recovery period, using constant or variable discharge pulse durations tx, gap durations ty, and/or pulse frequencies $f_D$, such that the entirety of the charge stored on the DC-blocking capacitors 55 is not continuously discharged through the patient's tissue, Rt, as occurs in post-program recovery period 99.

As noted earlier, pulsed discharge block 180 (FIG. 6A) can control the passive recovery circuitry to affect pulsed post-program recovery periods. This occurs by block 180 issuing various control signals at appropriate times corresponding to timing of the discharge pulses 101, which pulses as explained earlier can differ in their duration tx and in the duration ty of gaps 102 between them. As noted earlier, it is preferable that all passive recovery switches 96 be closed during each discharge pulse 101. This can be affected by pulsed discharge block 180 and recovery logic 176 of FIG. 6B in different ways, two of which are explained in FIG. 8.

In a first option (Op1) shown in FIG. 8, operation of the passive recovery switches 96 is enabled (EnRec='1'), and pulsed discharge block 180 asserts all of control signals Rec1-Rec17 during the discharge pulse 101 durations tx. In recovery logic 176 (FIG. 6B), this causes OR gate 182 to output a '1', and AND gate 184 to output a '1'. Because Rec1-Rec17 are asserted, all of OR gates 185 would also output a '1', and so each of AND gates 186 would output a '1' as control signals RCV1-RCV17. As noted earlier (see FIG. 3B), this closes all of the passive recovery switches 96 during the discharge pulse 101 durations tx. During gap 102 durations ty, Rec1-Rec17 are not asserted, and hence OR gates 185 would output a '0'. This would cause each of AND gates 186 to output a '0' as control signals RCV1-RCV17, thus opening all of the passive recovery switches 96 during the gaps 102.

In a second option (Op2) shown in FIG. 8, operation of the passive recovery switches 96 is again enabled (EnRec='1'), and pulsed discharge block 180 asserts AllOn during the discharge pulse 101 durations tx. In recovery logic 176 (FIG. 6B), this again this causes OR gate 182 to output a '1', and AND gate 184 to output a '1'. Moreover, because AllOn='1', all of OR gates 185 output a '1' regardless of the state of Rec1-Rec17. Thus, each of AND gates 186 would output a '1' as control signals RCV1-RCV17, which again closes all of the passive recovery switches 96 during the discharge pulse 101 durations tx. During gap 102 durations ty, Rec1-Rec17 are not asserted, and hence OR gates 185 would output a '0'. This would cause each of AND gates 186 to output a '0' as control signals RCV1-RCV17, thus opening all of the passive recovery switches 96 during the gaps 102.

To this point, pulsed post-program recovery periods 100, 100', 100" or like post-program periodic discharge periods, have been illustrated as being executed by pulsed discharge block 180 at the end of a stimulation program (such as SP1), and/or after an adjustment to such stimulation program. However, use of the disclosed pulsed post-program recovery periods are not limited to transitions in such stimulation programs, but may also be used more generally at the end of any generic IPG 10 program. This is shown in FIG. 9, in which a pulsed post-program recovery period 100, 100', 100", etc., is implemented at the end of a general IPG 10 program (such as P1 or P2) or between such general IPG 10 programs (such as between P1 and P2, or between P2 and P3). General IPG programs P1, P2, or P3 may comprise different operating modes of the IPG 10. For example, programs P1, P2, or P3 may comprise IPG maintenance programs or IPG test programs, which programs may or may not involve providing useful stimulation therapy to the patient. In one example, programs P1, P2, or P3 may comprise a program to test the resistance between various electrodes pairs 16 in the IPG 10, which as noted earlier is valuable to discern for different reasons. Such a resistance test program would normally comprise providing stimulation to the patient, but at levels that are preferably sub-threshold—i.e., not detectable by the patient.

To this point, it has been assumed that use of recovery control block 174 and its pulsed discharge block 180 will provide pulsed discharging of the DC-blocking capacitors 55 only after the end of a program, or between transitioning from one program to another. However, this technique is not so limited, and instead pulsed discharging may be used in other contexts, and during other time periods when the stimulation circuitry is not providing stimulation pulses.

Figure 10:
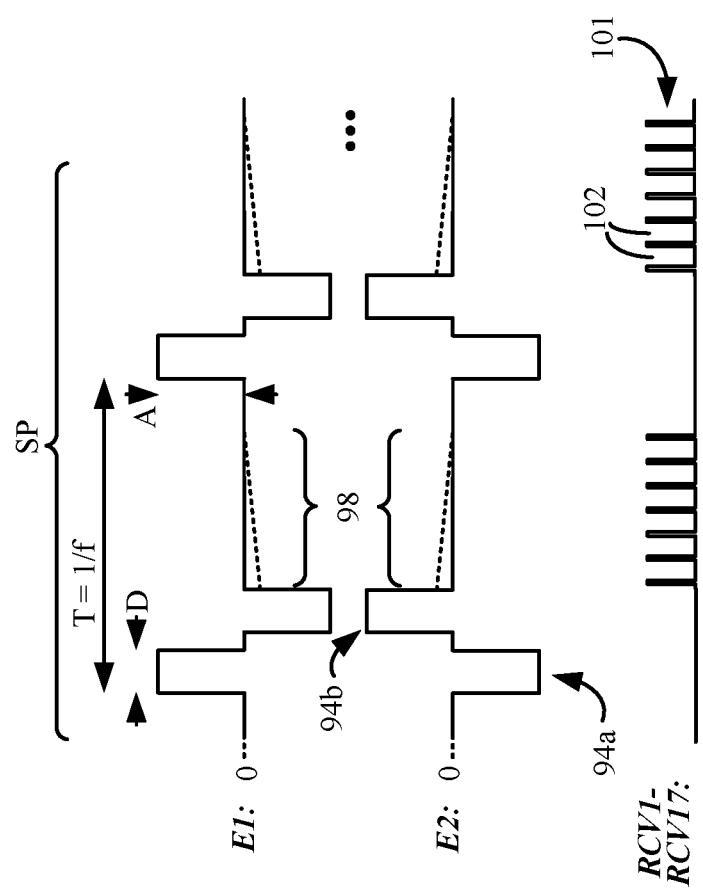
FIG. 10 shows use of pulsed discharging during a program and in particular between stimulation pulses of a program.

For example, pulsed discharge may occur in between stimulation pulses within a program, as shown in FIG. 10. FIG. 10 essentially mimics FIG. 3 discussed earlier, which shows a stimulation program of biphasic pulses being issued from electrodes E1 and E2. As explained earlier, a passive recovery period 98 follows each pulse (more specifically in this example, the second pulse phase 94*b*). However, pulse discharge block 180 (FIG. 6A) in this example controls the passive recovery switches 96*x* during the passive recovery periods 98 to periodically issue discharge pulses 101 with gaps 102 in between, similarly to what occurs during the pulsed post-program recovery periods illustrated earlier (FIG. 7). In other words, the passive recovery switches 96 are not held continually on during the passive recovery periods 98 as typically occurs, but are only on when passive recovery control signals RCV(x) are on during the discharge pulses 101. In the example shown, all recovery control signals RCV(x) are asserted in pulsed fashion during the passive recovery periods 98, and thus all passive recovery switches 96 are closed during those times. However, although not illustrated, the asserted control signals RCVx can be limited by pulsed discharge block 180 to those corresponding to the electrodes being stimulated (e.g., RCV1 and RCV2 for E1 and E2).

Using periodic discharge pulses 101 could be beneficial during passive recovery periods 98 between stimulation pulses for a number of different contexts. For one, although not illustrated, the stimulation pulses may not be biphasic, but instead may monophasic comprising just the first pulse phases 94*a* as illustrated in FIG. 4B. As the end of such a singular pulse phase, the charge on the DC-blocking capacitors may be significant, and hence risky to discharge using a continuously-on passive recovery period 98: a supra-threshold current may be generated in the patient tissue Rt for the reasons explained earlier. Using a pulsed discharge during period 98 would alleviate this concern.

While the improved passive recovery circuitry has been described as useful to recover charge from DC-blocking capacitors 55, this is not strictly necessary. Some IPG architectures may not use DC-blocking capacitors, yet may still have inherent capacitances that will charge as a stimulation current is provided. Such inherent capacitances may for example occur at various boundaries, such as the boundary between the electrodes and the patient's tissue. The improved recovery circuitry can be used to recover charge in such architectures, even though they lack intentionally-placed capacitances like the DC-blocking capacitors 55.

While disclosed in the context of an implantable pulse generator, it should be noted that the improved passive recovery circuitry could also be implemented in a non-implantable pulse generator, such as an External Trial Stimulator (ETS). See, e.g., U.S. Pat. No. 9,259,574 (describing an ETS).

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A pulse generator, comprising:
a plurality of direct current (DC) blocking capacitors;
a plurality of electrode nodes, wherein each electrode node is configured to be coupled to one of a plurality of electrodes in contact with a patient's tissue via one of the DC blocking capacitors;
a reference voltage;
a plurality of switches, wherein each of the switches is configured to couple the reference voltage to a different one of the electrode nodes;
stimulation circuitry configured to provide stimulation pulses to two or more of the electrode nodes; and
control circuitry configured to repeatedly close and open at least some of the plurality of switches during a time period when the stimulation circuitry is not providing stimulation pulses.

2. The pulse generator of claim 1, wherein the control circuitry is configured to select and repeatedly close and open only the switches coupled to the two or more electrode nodes during the time period.

3. The pulse generator of claim 1, wherein the control circuitry is configured to repeatedly close and open all of the switches during the time period.

4. The pulse generator of claim 1, wherein the control circuitry is configured to repeatedly close and open the at least some of the plurality of switches at a constant frequency during the time period.

5. The pulse generator of claim 1, wherein the control circuitry is configured to repeatedly close the at least some of the plurality of switches for a duration that varies over the time period.

6. The pulse generator of claim 1, wherein the control circuitry is configured to repeatedly close and open the at least some of the plurality of switches at a variable frequency during the time period, but wherein the control circuitry is configured to repeatedly close the at least some of the plurality of switches for a duration that is constant over the time period.

7. The pulse generator of claim 1, wherein the control circuitry is configured to repeatedly open the at least some of the plurality of switches for a duration that varies over the time period.

8. The pulse generator of claim 1, wherein the stimulation circuitry is configured to provide the stimulation pulses to two or more of the electrode nodes during a program, and wherein the control circuitry is configured to repeatedly close and open the at least some of the plurality of switches after an end of the program.

9. The pulse generator of claim 1, wherein the time period occurs between two successive stimulation pulses provided to the two or more of the electrode nodes.

10. The pulse generator of claim 1, further comprising a plurality of resistors, wherein each of the resistors is serially connected to one of the switches between one of the electrodes nodes and the reference voltage.

11. The pulse generator of claim 10, wherein the control circuitry is further configured to vary a resistance of the plurality of resistors.

12. The pulse generator of claim 1, further comprising a battery, wherein the reference voltage comprises a voltage of the battery.

13. The pulse generator of claim 1, further comprising a conductive case, wherein at least one of the electrode nodes comprises a case electrode node configured to be coupled to the conductive case.

14. The pulse generator of claim 1, further comprising at least one implantable lead, wherein the electrodes are located on the at least one implantable lead.

15. A pulse generator, comprising:
a plurality of direct current (DC) blocking capacitors;
a plurality of electrode nodes, wherein each electrode node is configured to be coupled to one of a plurality of electrodes in contact with a patient's tissue via one of the DC blocking capacitors;
stimulation circuitry configured to provide stimulation pulses to a selected two or more of the electrode nodes during a stimulation program;
a reference voltage;
a plurality of switches, wherein each of the switches is configured to couple the reference voltage to a different one of the electrode nodes; and
control circuitry configured to repeatedly close and open the plurality of switches at an end of the stimulation program when the stimulation circuitry is not providing stimulation pulses.

16. The pulse generator of claim 15, wherein the control circuitry is configured to repeatedly close and open the plurality of switches at a constant frequency.

17. The pulse generator of claim 15, wherein the control circuitry is configured to repeatedly close the plurality of switches for a duration that varies, or wherein the control circuitry is configured to repeatedly open the plurality of switches for a duration that varies.

18. The pulse generator of claim 15, further comprising a plurality of resistors, wherein each of the resistors is serially connected to one of the switches between one of the electrodes nodes and the reference voltage, wherein the control circuitry is further configured to vary a resistance of the plurality of resistors.

19. The pulse generator of claim 15, further comprising
a battery, wherein the reference voltage comprises a voltage of the battery; and
a conductive case, wherein at least one of the electrode nodes comprises a case electrode node configured to be coupled to the conductive case.

20. The pulse generator of claim 15, further comprising at least one implantable lead, wherein the electrodes are located on the at least one implantable lead.

* * * * *